United States Patent [19]

Michael et al.

[11] Patent Number: 5,591,433
[45] Date of Patent: Jan. 7, 1997

[54] ORAL ADMINISTRATION OF IMMUNOLOGICALLY ACTIVE BIOMOLECULES AND OTHER THERAPEUTIC PROTEINS

[75] Inventors: J. Gabriel Michael; Allen Litwin, both of Cincinnati, Ohio

[73] Assignee: University of Cincinnati, Cincinnati, Ohio

[21] Appl. No.: 405,604

[22] Filed: Jan. 20, 1995

Related U.S. Application Data

[63] Continuation of Ser. No. 994,932, Dec. 22, 1992, abandoned, which is a continuation-in-part of Ser. No. 719,160, Jun. 21, 1991, abandoned.

[51] Int. Cl.$^6$ .......................... A61K 39/00; A61K 9/16; A61K 13/00; A61K 45/00
[52] U.S. Cl. ..................... 424/184.1; 424/464; 424/482; 424/497; 424/422; 424/451; 424/278.1; 424/275.1; 424/274.1
[58] Field of Search .......................... 424/184.1, 275.1, 424/464, 482, 497, 422, 451, 274.1, 278.1

[56] References Cited

U.S. PATENT DOCUMENTS

| | | |
|---|---|---|
| 3,143,473 | 8/1964 | Hennessen et al. . |
| 3,458,621 | 7/1969 | Tint . |
| 3,767,790 | 10/1973 | Guttag . |
| 3,823,228 | 7/1974 | Ferris et al. . |
| 3,860,490 | 1/1975 | Guttag . |
| 3,909,444 | 9/1975 | Anderson et al. . |
| 4,016,254 | 4/1977 | Seager et al. . |
| 4,017,647 | 4/1977 | Ohno et al. . |
| 4,269,764 | 5/1981 | Patterson et al. . |
| 4,348,384 | 9/1982 | Horikoshi et al. . |
| 4,469,677 | 9/1984 | Michael et al. . |
| 4,507,276 | 3/1985 | Tencza et al. . |
| 4,642,232 | 2/1987 | Yman . |
| 4,704,295 | 11/1987 | Poter et al. . |
| 4,774,226 | 9/1988 | Lewenstein . |
| 4,794,000 | 12/1988 | Ecanow . |
| 4,798,844 | 1/1989 | Fujita et al. . |
| 4,820,627 | 4/1989 | McGeehan et al. . |
| 4,874,613 | 10/1989 | Hsiao et al. . |
| 4,900,557 | 2/1990 | Dell et al. . |
| 4,920,209 | 4/1990 | Davis et al. . |
| 4,946,945 | 8/1990 | Wojdani . |
| 4,981,693 | 1/1991 | Higashi et al. . |
| 4,996,058 | 2/1991 | Sinnreich et al. . |
| 5,032,405 | 7/1991 | Huang et al. . |
| 5,047,258 | 9/1991 | Belanger et al. . |
| 5,049,390 | 9/1991 | Wojdani . |
| 5,116,612 | 5/1992 | Wojdani . |
| 5,160,742 | 11/1992 | Mazer et al. . |
| 5,202,159 | 4/1993 | Chen et al. . |
| 5,236,713 | 8/1993 | Wato et al. . |

FOREIGN PATENT DOCUMENTS

| | | |
|---|---|---|
| B52792/90 | 3/1989 | Australia . |
| 621398 | 2/1963 | Belgium . |
| 0035780 | 9/1981 | European Pat. Off. . |
| 0135022 | 3/1985 | European Pat. Off. . |
| 0192321 | 1/1986 | European Pat. Off. . |
| 0278877 | 8/1988 | European Pat. Off. . |
| 0277741 | 8/1988 | European Pat. Off. . |
| 56-142211 | 11/1981 | Japan . |
| 2178313 | 7/1986 | United Kingdom . |
| WO8606635 | 11/1986 | WIPO . |
| WO8908449 | 9/1989 | WIPO . |
| WO90/004963 | 5/1990 | WIPO . |
| WO9116882 | 11/1991 | WIPO . |
| 9206708 | 4/1992 | WIPO . |
| 9205778 | 4/1992 | WIPO . |

OTHER PUBLICATIONS

Lee et al: *Biotechnology & Bioengineering*, vol. 40, pp. 207–213 (1992).

Yoshimura et al: *Arch Otolaryngol Head Neck Surg.*, vol. 117, pp. 889–894 (Aug. 1991).

Lin et al: *J. Microencapsulation*, vol. 8, No. 3, 317–325 (1991).

*Drugs and the Pharmaceutical Sciences*, vol. 36, Aqueous Polymeric Coatings for Pharmaceutical Dosage Forms, Chapter 2, pp. 9445–114, "Application of Eudragit E 30 D In Controlled–Release Coatings" by Isaac Chebre–Sellassie and Russell U. Nesbitt. ©1989.

Henderson, D. C., D. M. Moran & A. W. Wheeler, *Differential Suppressive Influence of Intranasal Application of Rye Grass Pollen Extract on IgE Antibody Production in the Mouse*, Clin. Exp. Immunol. (1985) 59, pp. 343–350.

Henderson, D. C., A. W. Wheeler, D. M. Moran, *Suppression of Murine IgE Responses with Amino Acid Polymer/Allergen Conjugates*, Int. Archs Allergy appl. Immun. 82: 208–211 (1987).

Henderson, D. C., D. M. Moran, *Antibody Responses of Mice to Intragastric and Parenterally Administered Aeroallergens*, Int. Archs Allergy appl. Immun. 79: 66–71 (1986).

(List continued on next page.)

*Primary Examiner*—James C. Housel
*Assistant Examiner*—N. M. Minnifield
*Attorney, Agent, or Firm*—Wood, Herron & Evans, P.L.L.

[57] ABSTRACT

An orally administrable therapeutic protein is provided by combining the therapeutic protein with a stabilizing agent in an aqueous solution. The solution is coated onto nonpareils and microencapsulated with a water emulsifiable enteric coating composition. The microcapsules are orally administered. The coating protects the protein as it passes through the stomach. Upon reaching the small intestines, the basic pH of the intestinal juices will dissolve the coating, allowing the protein to be released and induce antigen specific immune response which has the specificity of the native molecule. The stabilizing agent protects the therapeutic protein from denaturation during the encapsulation process. In addition to being immunogenic, when administered orally, encapsulated allergen has a therapeutic effect in the treatment of human allergies.

25 Claims, 5 Drawing Sheets

OTHER PUBLICATIONS

Wheeler, A. W., D. C. Henderson, L. J. F. Youlten, I. I. Al-Janabi, B. E. Hickman, I. H. Taylor, D. M. Moran, *Immunogenicity in Guinea Pigs and Tolerance in Grass Pollen–Sensitive Volunteers of Enteric–Coated Grass Pollen Allergens,* Int. Archs Allergy appl. Immun. 83: 354–358 (1987).

Horak, F., A. W. Wheeler, *Oral Hyposensitisation with Enteric–Coated Allergens as Extension Therapy Following a Basic Subcutaneous Course of Injections,* Int. Archs Allergy appl. Immun. 84: 74–78 (1987).

Fukumori et al. Chem. Pharm. Bull. 35(7): 2949–2957, 1987.

Wong, George K., Development of Novel Oral Enteric–Coated Aquaculture Vigro Vaccines (1990) (unpublished Ph.D. thesis, Oregon State University, available from UMI Dissertation Services).

Moldoveanu et al., 1993. J. Infect. Disease 167:84–90.

Wheeler et al., 1987. Int. Arch. Allergy Appl. Immunol. 83(4):354–8.

Lai, 1985. Diss. Abs. Int. 49(10B):4254.

Waldman et al., 1986. Amer. J. Med. Sci. 292(6):367–71.

Fukumori, et al., 1988(a). Chem. Pharm. Bull. 36(12):4927–32.

Fukumori, et al., 1988. Chem. Pharm. Bull. 36(8):3070–78.

Wong, 1990. Diss. Abs. Int. 52(5B):2519.

Langer, et al., 1990. Science 249:1527–1533.

Murray, et al., 1990. Aus. J. Hospital Pharm. 20(3):235–38.

FIG. 1

(Graph: ANTI OVA IgG ANTIBODY TITER vs DAYS)
- HPMAS COATED MICROSPHERES FED ON DAYS -5, -4 & -3
- GRND MICROSPHERES
- OVA + LACTOSE (UNCOATED)

FIG. 5

(Graph: ANTIRAGWEED IgG ANTIBODY TITER vs DAYS)
- RYEGRASS MICROSPHERES
- NO CHALLENGE
- i.p. PRIMING WITH RYEGRASS (at day -14)

5,591,433

ORAL ADMINISTRATION OF IMMUNOLOGICALLY ACTIVE BIOMOLECULES AND OTHER THERAPEUTIC PROTEINS

This is a continuation of application Ser. No. 07/994,932, filed Dec. 22, 1992, abandoned, which is a continuation-in-part of application Ser. No. 07/719,160, filed Jun. 21, 1991 now abandoned, entitled "Orally Administrable Therapeutic Proteins and Method of Making."

BACKGROUND OF THE INVENTION

Immune response in mammals, including humans, is most predictably induced by parenteral (injectable) administration of a protein antigen. Oral administration of a protein antigen is usually an ineffective route of immunization. Indeed, oral administration of a protein may be immunosuppressive rather than immunogenic (Mowat, A. M. 1987, "The Regulation of Immune Responses to Dietary Protein Antigens," *Immunol. Today*, 8:93). Thus, development of a method for efficient oral immunization would be extremely desirable. Immunization has beneficial therapeutic effects in many areas of clinical medicine. Specifically, antimicrobial vaccines consisting of bacteria, viruses and their products are beneficial in preventing and combating infections. Also, allergy immunotherapy, a treatment in which injections of small doses of allergens results in alleviation of allergy symptoms, is important in therapy of inhalant allergies and anaphylaxis. Finally, treatment of autoimmune diseases with autoantigens or their components can alleviate the autoimmune disease.

Collectively, we refer to these proteins as therapeutic since they exert a therapeutic effect through activating the immune system of humans and mammals. These therapeutic proteins are all susceptible to proteolytic enzymatic digestion.

Immunization by oral administration of therapeutic proteins has been quite ineffective in the past. It is believed that these proteins are damaged or destroyed by gastric and intestinal juices, thus losing their immunogenicity by the time they reach the lymphoid (immune) tissue in the gastrointestinal tract.

SUMMARY OF THE INVENTION

The present invention is premised on the realization that an orally administrable therapeutic proteins can be formed by microencapsulating the protein with a coating which is insoluble under acid conditions and resistant to proteolytic digestion. Such conditions are encountered in the mammalian stomach and part of the small intestines. Preventing exposure to acid and proteolytic digestion preserves antigenic structure of the protein and its ability to immunize.

The present invention is further premised on the realization that by microencapsulating the protein under totally aqueous conditions without employing any nonaqueous solvents, the structure and the immunogenicity of the protein remains intact.

More particularly, the present invention is premised on the realization that the therapeutic proteins should be coated with an acid stable coating under totally aqueous conditions so that they can pass through the stomach without being digested and then released intact into the small intestines where they can exert their therapeutic and/or immunological activity. In a preferred embodiment, the enteric coating is a water emulsion of ethylacrylate methylacrylic acid copolymer, or hydroxypropyl methyl cellulose acetate succinate (HPMAS).

The objects and advantages of the present invention will be further appreciated in light of the following detailed description and drawings.

BRIEF DESCRIPTION OF THE DRAWINGS

FIG. 1 is a graph depicting anti-OVA (hen egg albumin) IgG antibody titers of mice fed hydroxypropylmethyl cellulose acetate succinate (HPMAS) coated OVA containing microspheres or ground coated OVA microspheres or OVA in solution;

FIG. 5 is a graph showing IgG antibody response following oral administration of ryegrass containing enteric coated microspheres in ryegrass primed mice;

DETAILED DESCRIPTION

Figure 2:
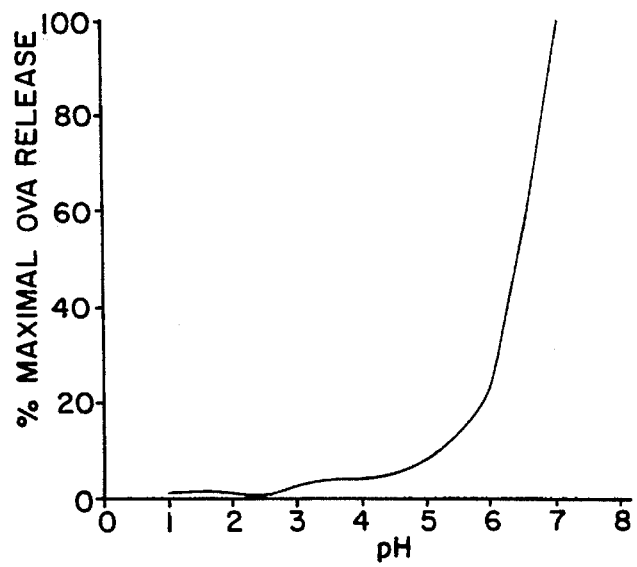
FIG. 2 is a graph depicting the release of hen egg albumin (OVA) from enteric coated microspheres after two hours in solutions at various pH.

According to the present invention, an orally administrable therapeutic agent such as a protein or protein containing virus or bacteria is formed by microencapsulating the therapeutic agent with an enteric coating. This is generally referred to as the therapeutic protein.

The therapeutic agents are dispersed in an aqueous solution. The aqueous solution is then sprayed onto nonpareils. Subsequently the microspheres are coated with a water emulsion of a polymer which upon solidification is acid resistant. This protects the therapeutic protein as it passes through the stomach and releases it into the small intestines where it can act upon the lymphoid tissue.

For the purpose of the present invention, therapeutic protein will include allergenic proteins and digested fragments thereof. These include pollen allergens from ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple, elm, etc., dust and mites, bee venom, food allergens, animal dander, and other insect venoms.

Further, any of these allergens digested according to the method disclosed in U.S. Pat. No. 4,469,677, the disclosure of which is incorporated herein by reference, are also suitable for use in the present invention. This basically discloses the proteolytic enzymatic digestion of allergens. Accordingly, polypeptides formed by such proteolytic enzymatic digestion are also suitable for use as therapeutic proteins for use in the present invention.

Other therapeutic proteins include microbial vaccines which include viral, bacterial and protozoal vaccines and their various components such as surface antigens. These include vaccines which contain glycoproteins or proteins. Such vaccines are prepared from *Staphylococcus aureus, Streptococcus pyogenes, Streptococcus pneumoniae, Neisseria menmgitidis, Neisseria gonorrhoeae*, Salmonellae species, Shigellae species, *Escherichia coli*, Klebsiellae species, Proteus species, *Vibrio cholerae, Helicobacter pylori, Pseudomonas aeruginosa, Haemophihts influenzae, Borderella pertussis, Branhamella catarrhalis, Mycobacterium tuberculosis, Legionella pneumophila, Pneumocystis carinii, Treponema pallidum* and Chlamydiae species, tetanus toxoid, diphtheria toxoid, influenza viruses, adenoviruses, paramyxoviruses, rubella viruses, polioviruses, hepatitis viruses, herpesviruses, rabies viruses, HIV-1 viruses, HIV-2 viruses, and papilloma viruses. Other therapeutic proteins suitable for use in the present invention include insulin, human growth factor, myelin basic proteins, collagen S antigen, transforming growth factor beta. These proteins are generally available in lyophilized or ligand form.

A second component which can be added to the therapeutic protein is a stabilizing agent. Stabilizing agents provide physical protection for the protein. Generally these stabilizing agents are therapeutically inactive water soluble sugars such as lactose, mannitol and trehalose. These act to protect the therapeutic antigen during the coating process.

To form orally administrable microcapsules for use in the present invention, an aqueous solution of the therapeutic protein and the optional stabilizing agent is formed. The aqueous solution will include generally from about 0.5 to about 10% by weight of the therapeutic protein with about 1% being preferred, and from about 1% to about 10% by weight of the stabilizing agent with about 5% being preferred. If the protein solution has a low viscosity, it may be desirable to add 1–10% of polyvinylpyrrolidone to bind the therapeutic protein to the nonpareil.

Nonpareils are small, round particles of pharmaceutically inert materials. Generally nonpareils formed from the combination of sucrose and starch are preferred. One such brand is Nupareils which is sold by Ingredient Technology Corporation. The preferred size is 30–35 mesh.

The nonpareils are coated with an amount of the aqueous solution to provide a coating of 1–10% protein by weight on a solids basis. Glatt brand powder coater granulators such as the GPCG-1, GPCG-5, or GPCG-60 fluid bed coaters are suitable for use in this application. Coating conditions and times will vary depending on the apparatus and coating viscosity. But, generally all coating steps must be conducted at less than 50° C., preferably less than 35° C. to avoid denaturing the protein.

The protein coated microspheres are dried and subsequently coated with an acid stable polymer (enteric coating). Generally, the coating will be applied in the same manner as the protein with the same equipment.

The coating composition used in the present invention is preferably a water based emulsion polymer. The preferred coating is an ethylacrylate methacrylic acid copolymer sold under the trademark Eudragit L 30D manufactured by Rhom Pharma. This has a molecular weight of about 250,000 and is generally applied as a 30% aqueous solution. An alternate coating is hydroxypropylmethyl cellulose acetate succinate.

The coating composition can be combined with a plasticizer to improve the continuity of the coating. There are several well known plasticizers typically used. Triethylcitrate (TEC) sold by Morfley Inc. is preferred. This can form about 1–30% of coating composition. Although plasticizers can be liquid, they are not considered to be solvents since they lodge within the coating altering its physical characteristics. They do not act to dissolve the protein. Any plasticizer which dissolves or denatures the protein would be unacceptable.

Talc (3.0% of coating composition) can also be added to prevent sticking between the particles if desired. Also, an antifoaming agent (0.0025 % of coating composition) such as sorbitan sesquioleate (Nikko Chemicals Company Limited) or silicone can be added. Both the talc and antifoaming agent are added only if needed.

The microspheres coated with the therapeutic protein and optional stabilizing agents, are dried and are then coated with the enteric coating as previously described. The coating solution is about 30% polymer, 0–30% plasticizer, 0 to 3% talc and 0 to 0.0025 % antifoaming agent and water. It is important that there be no organic solvents including alcohols and even glycols present in the coating composition. The presence of these solvents during coating application can denature the therapeutic protein. The coating is conducted in the same equipment used to coat the nonpareils with therapeutic protein. The temperature for this coating should be about 30° C. but less than 50° C.

In an alternate embodiment of the present invention, a therapeutically acceptable water dispersible aluminum compound such as aluminum sulfate or aluminum hydroxide is added to the aqueous dispersion or solution of protein prior to coating onto the nonpareil. This acts to increase immunogenicity of the proteins. Generally 1% to 10% of aluminum compound is added.

The enteric coated microspheres then can be placed in gel capsules for oral administration to humans. Dosage will depend on the individual and the course of the therapy. For example, in treatment with ragweed microspheres, the dosage would be 0.03 to 35 units in terms of a major allergenic protein, Arab a 1, administered daily. This is similar to the dosage used in immunotherapy by injections.

The invention will be further appreciated in light of these following examples.

EXAMPLE 1

Immunogenicity of Encapsulated OVA

Immunological properties of OVA released from microspheres were tested following oral administration to 6–8 weeks old BDF mice. Control groups of mice were fed with unencapsulated OVA (OVA and lactose) or ground enteric coated microspheres. The enteric coating was hydroxy propyl methyl cellulose acetate succinate sold by Shin Etsu Chemical Company which was applied in an aqueous suspension. (10% HPMCAS, 2.8% TEC, 3.0% talc, 0.0025% Sorbitan Sesquioleate.)

The OVA preparations were fed to BDF mice as described in FIG. 1. Subsequently the mice were bled and their serum anti OVA IgG antibody levels determined by ELISA (Emguall, E., Perlman, P., 1972, "Enzyme Linked Immunosorbant Assay ELISA III Quantitation of Specific Antibodies by Enzyme Labeled Anti-immunoglobulin in Antigen Coated Tubes," *J. Immunol.*, 109:129). As shown in FIG. 1, oral administration of encapsulated OVA resulted in significant immune response to the specific antigen. Unencapsulated OVA antigens were not immunogenic.

EXAMPLE 2

Properties of Encapsulated OVA

Figure 3:
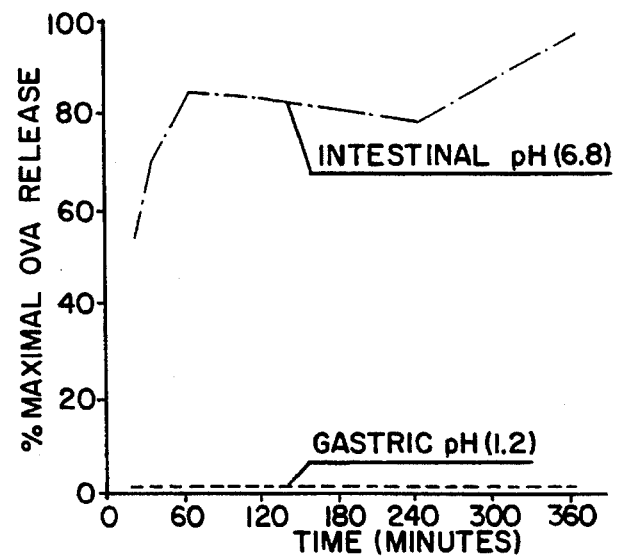
FIG. 3 is a graph depicting OVA released over time from enteric coated microspheres in solutions at gastric (1.2), or intestinal pH (6.8)

OVA coated nonpareils were prepared from 20 grams of nonpareils, 1 gram of OVA, and 1 gram of lactose. These were then coated with Eudragit L30D in a total aqueous system (7 grams Eudragit L30D and 22 grams coated nonpareils). These were initially tested to determine resistance to acid pH typically encountered in the gastric juices. As shown in FIG. 2, the OVA was not released until the pH approached 6. At pH 6 to 7, substantially all of the OVA was released. To determine the release of OVA over time, these microspheres were exposed to either intestinal pH of 6.8 or gastric pH of 1.2 (FIG. 3). At the gastric pH of 1.2, virtually none of the OVA was released for 6 hours. However, at pH 6.8, substantially all of the OVA was released in a short time. OVA released from the microspheres was tested for antigenicity and immunogenicity. It was demonstrated that the released antigen retained its native structure (RAST inhibition assay), and was as immunogenic as the untreated OVA (data not shown). Immune responses to all therapeutic antigens described below were always measured against native antigens by RAST assay, thus proving that the encapsulated antigens retained their native structure.

EXAMPLE 3

Immunogenicity of Encapsulated OVA

Figure 4:
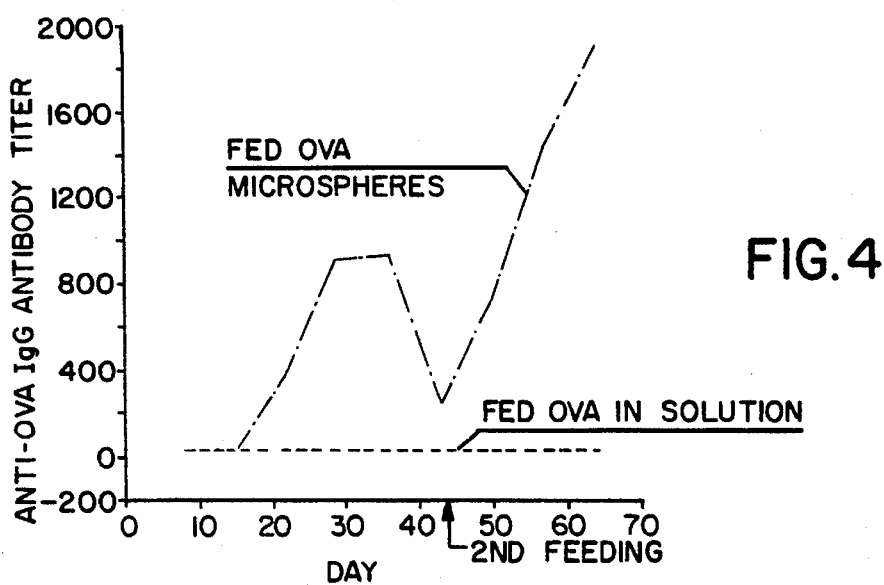
FIG. 4 is a graph showing IgG antibody response to OVA in naive mice following the feeding with OVA (1 milligram per day for 3 days) as enteric coated microspheres or OVA in solution.

The enterocoated microspheres containing OVA as described above were fed to 6–8 weeks old female BDF mice, (1 mg OVA per day or 3 days in microspheres or alternately in solution). Anti-OVA antibody tiler (IgG) of the mice fed OVA microspheres coated with Eudragit L30D rose significantly after the 3 days feeding and continued to rise after a second feeding at day 42. Mice fed OVA in solution did not develop antiOVA antibodies. The results are shown in FIG. 4.

EXAMPLE 4

Immunogenicity of Encapsulated Perennial Rye Grass Allergen

Perennial ryegrass allergen coated nonpareils were prepared from 20 grams nonpareils, 1 gram allergen, 1 gram lactose. These were coated with Eudragit L30D in a totally aqueous system (7 grams Eudragit L30D and 22 grams coated nonpareils) and orally administered to mice.

Groups of female BDF mice 6–8 weeks old were immunized on day minus 14 with 100 micrograms of perennial ryegrass (IP in alum). On day 0, mice were placed into two treatment groups, the first group was fed enteric coated ryegrass containing in microspheres, 1 milligram of ryegrass per mouse given on days 1, 2, and 3, the second group was given no postpriming treatment. The mice were bled weekly and the total IgG anti-ryegrass titer was determined by ELISA. The mice that received the microencapsulated ryegrass generated a strong antiryegrass IgG antibody response compared to mice that were not fed. The results are shown in FIG. 5.

EXAMPLE 5

Immunogenicity of Encapsulated Ragweed in Mice

Figure 6:
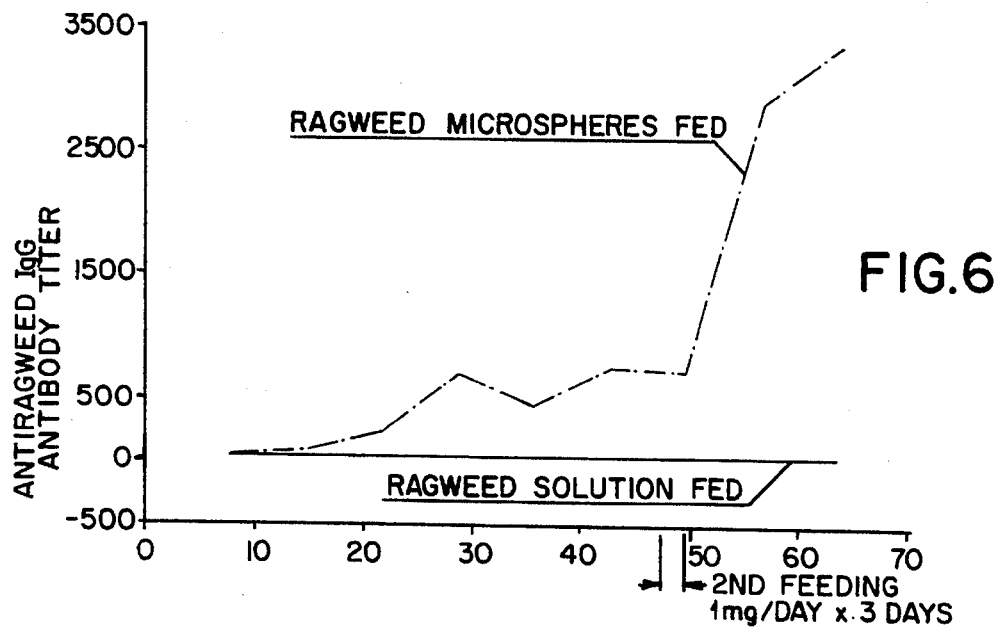
FIG. 6 is a graph showing IgG antibody response to ragweed in mice following oral administration of ragweed containing microspheres or ragweed in solution.

Ragweed allergen coated nonpareils were prepared from 20 grams nonpareils, 1 gram allergen, and 1 gram lactose. These were coated with Eudragit L30D in a totally aqueous system (7 grams Eudragit L30D and 22 grams coated nonpareils) and orally administered to BDF mice 6–8 week old females. In the initial feeding, microspheres containing 1 milligram ragweed per day for 3 days were administered to the animals. A second feeding of 1 milligram ragweed per day for 3 days was given at days 47–50. A control group of mice were fed ragweed solution at above described amounts and dates. As shown in FIG. 6, the mice fed ragweed bound to the microspheres and encapsulated with Eudragit L30D showed significant antiragweed IgG antibody titers whereas mice fed the ragweed solution did not show any increase in antibody titer.

EXAMPLE 6

HUMAN STUDIES

1. Preparation of Microspheres With Ragweed

Microencapsulated ragweed microspheres were prepared as follows:

The ragweed solution was formed by dissolving 203 grams of polyvinylpyrrolidone and 203 grams lactose in 2439.6 grams of sterile water (50° C.). Next, 34.4 grams of lyophilized short ragweed extract obtained from Greer Laboratories, Lenoir, N.C., was added and dissolved at room temperature.

The coating solution was formulated by combining 4068 grams of Eudragit L30D (30% solids) with 122 gram triethyl citrate.

The microspheres were formed in a Glatt model GPCG-5 Wurster spray dryer. The Wurster was set up according to the following specifications:

Spray Nozzle
 Port Size: 1.2 Atomization air: 20 BAR
 Port Height: ⅜" Inlet flap: open
 Angle: flush The Wurster chamber was loaded with 2000 grams of 30–35 mesh nonpareils. The inlet air pressure was adjusted such that the microspheres reached a "fluidized" state. The inlet air temperature was increased till the product temperature was between 40°–45° C. Spray and atomization-air hoses were connected and the antigen solution was sprayed at a relatively slow rate (10–13 gms/min). The variables of air flow ("outlet flap"), inlet air temperature, and spray rate were adjusted in order to maintain a free "fluidized" state of the microspheres. Throughout the process, the spray rate was gradually increased to the point where it became impossible to achieve a free fluidized state of the particles without raising the product temperature above the desired range (40°–45° C.). When all of the antigen solution was sprayed, the spray and atomization hoses were disconnected and the inlet air temperature was decreased to allow the product to cool (37°–38° C.). Spray and atomization-air hoses were reconnected and the enteric coating (Eudragit L30D) was sprayed (initially at around 30 gms/min) again adjusting variables of inlet air temperature and air flow to achieve maximum spray rate while maintaining a product temperature of 29°–32° C. At the end of the coating process, spray and atomization-air hoses were disconnected, the inlet air temperature and air flow is adjusted to achieve a product temperature of 55°–60° C. and the fluidized particles cured at this temperature for 1h. Following the curing step, the inlet air temperature was decreased and the particles allowed to cool to below 45° C. The finished product was collected and the yield calculated.

2. Immunogenicity of Ragweed Microspheres in Humans

Nine volunteers selected for this study were all in good general health. All volunteers were judged to be ragweed sensitive based on their report of seasonal symptoms, intradermal end point skin testing, and the presence of ragweed specific IgE antibodies in their serum as determined by an enzyme based RAST analysis.

sensitization occurs, an individual will become symptomatic when there is an exposure to the allergen. Exposure to the allergen usually results in an increase of IgE antibody in the circulation of the allergic individual. Successful immunotherapy results in blunting of such secondary IgE response which may also contribute to the alleviation of allergy symptoms (Creticos, P. S., 1992, "Immunologic Changes Associated with Immunotherapy," *Immunol. Aller. Clin. N. American,* 12:13).

We measured levels of ragweed specific IgE antibodies at the start and the end of the ragweed season by RAST (Hoffman, D., 1979, "The Use and Interpretation of RAST to Stinging Insert Venom," *Ann. Allergy,* 42:224) in treated and control ragweed sensitive individuals. As shown in Table 1, treated patients had significantly lower rise in ragweed specific IgE antibodies during their seasonal exposure to ragweed than the untreated control patients.

TABLE 1

| | Blunting of The IgE Response During The Ragweed Season | | |
|---|---|---|---|
| | Mean IgE Titer At The Start Of The Ragweed Season | Mean IgE Titer At The End Of The Ragweed Season | Mean Percent Increase In IgE During The The Ragweed Season |
| Controls (n = 9) | 54.7 | 89.9 | 64.3 |
| Treatment Group (n = 9) | 69.7 | 81.0 | 16.2 |

Subjects were given daily doses of encapsulated short ragweed. Dosages were increased every 2 days if no adverse reaction occurred. The highest dose of encapsulated ragweed achieved in the term of Amb a 1 antigen content was 20–30 u/day (FDA Potency Test on Amb a 1 §680.4 of Title 21 of the Food and Drug Administration). This dosage is comparable to the dosage given the patients subcutaneously in standard immunotherapy (Van Metre, T. E., Jr., Adkinson, N. F., Jr.: "Immunotherapy for Aeroallergen Disease in Middleton," Reed C. E., Ellis F. F. Adkinson N. F. Jr. et (eds): "Allergy Principles and Practice", Ed. 3, Vol. II, St. Louis, C. V. Moshy, 1988, p. 1336). Blood samples were obtained weekly or bi-weekly. Subjects received an average of 43 doses of encapsulated short ragweed. They were kept on a maintenance dose three days per week throughout the ragweed season.

A course of effective immunotherapy is usually associated with an increase in the allergen specific IgG antibody titer in the patient's serum (Creticos, P. S., 1992, "Immunologic Change Associated with Immunotherapy," *Immunol. Aller. Clin. N. American,* 12:13). Therefore, sera from subjects on this study were assayed for short ragweed specific IgG antibody titers by an enzyme linked immunosorbent assay (ELISA). Patients receiving the encapsulated short ragweed showed a significant increase in anti-ragweed specific serum IgG titers prior to and during the season. In contrast, sera from untreated ragweed sensitive controls showed little change in the anti-ragweed specific IgG titers throughout the study.

Figure 7:
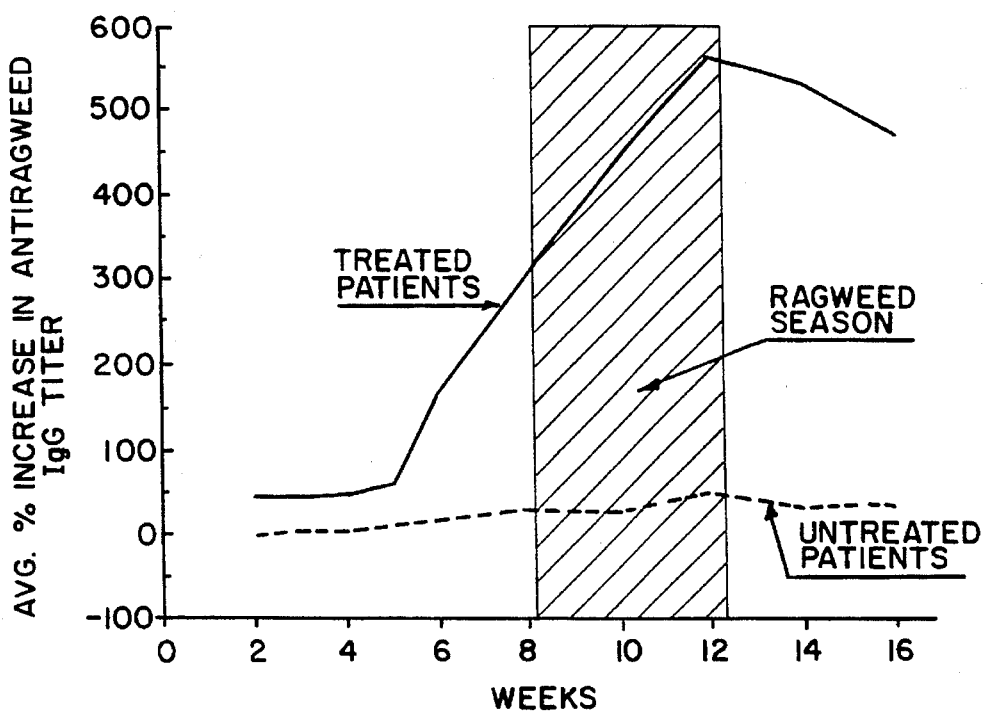
FIG. 7 is a graph showing IgG antibody titers of humans who were allergic to ragweed and were given orally enteric coated ragweed before and during ragweed season compared to a ragweed allergic control group.

FIG. 7 shows the influence of the treatment on ragweed specific IgG antibody levels prior to, during and following ragweed season.

3. Blunting of the IgE Response During the Ragweed Season

Figure 8:
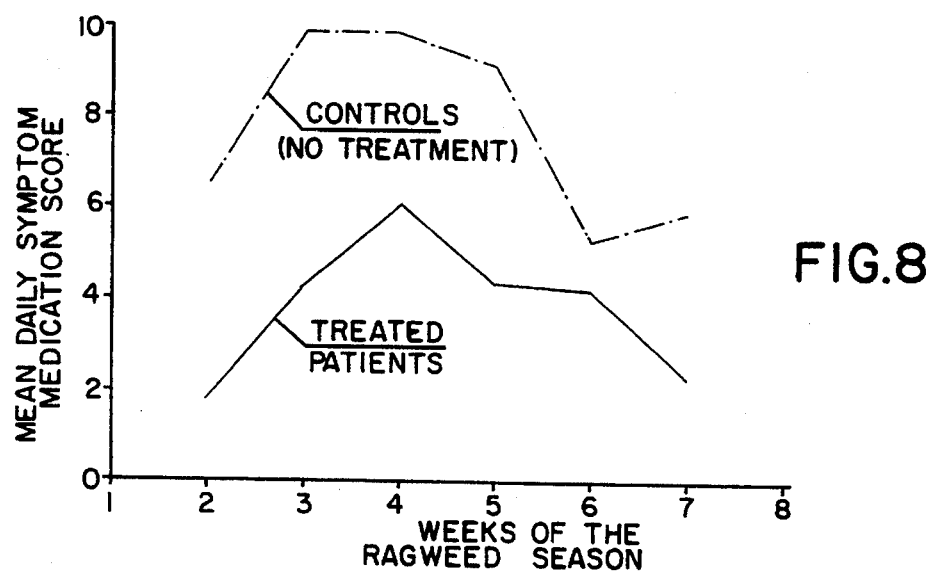
FIG. 8 is a graph showing mean symptoms and medication scores for the orally treated ragweed allergic patients with enteric coated ragweed and control ragweed allergic group given no treatment.

Allergen specific IgE antibodies seem to play an important role in sensitizing mast-cell-mediator pathways. Once 4. Clinical Efficacy of Oral Immunotherapy To establish clinical efficacy of the present invention, the ragweed sensitive patients, both the control group and the treated group were evaluated for severity of symptoms during the ragweed season. Each subject graded his symptoms for each 12-hr period, 12 noon until midnight and from midnight until 12 noon. Separate ratings were given for sneezing; stuffy nose; red itchy eyes; coughing; and number of antihistamine tablets taken. Each system was graded on a scale of 0–3: 0, no symptoms; 1, symptoms for less than 30 min; 2 symptoms for 30 min to 2 hr; and 3, symptoms for more than 2 hr. The number of antihistamine tablets taken was added to the total symptom score to arrive at a daily total symptom-medication score for each patient. These respective numbers were totaled and the mean averages computed. A graph showing the symptom medication scores of this study is set forth in FIG. 8. The control group had significantly higher numbers of symptoms than the treated group indicating the therapeutic value of the treatment. These results also confirm a correlation between IgG antibody titers and therapeutic effects of the treatment.

EXAMPLE 7

Immunogenicity of Microspheres Containing Bovine Serum Albumin in Mice

Figure 9:
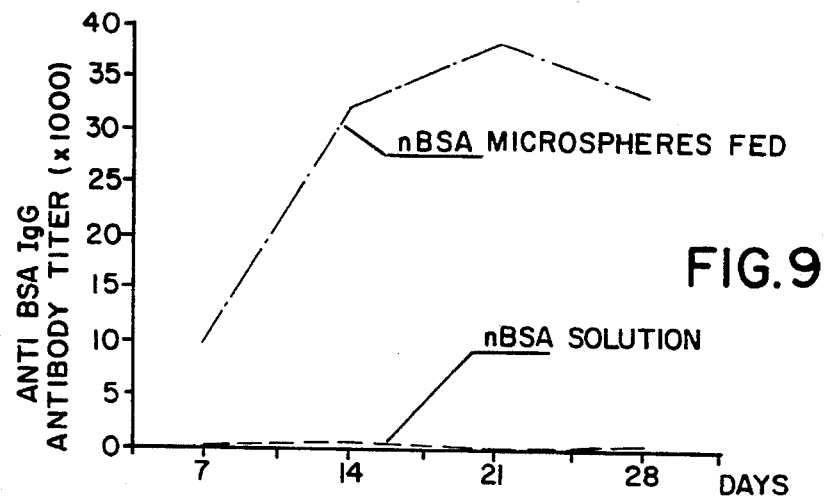
FIG. 9 is a graph showing IgG antibody titer of mice fed nBSA solution or nBSA enteric coated microspheres.

Nonpareils were coated with an aqueous solution of bovine serum albumin (nBSA) and subsequently coated with Eudragit L30D in a totally aqueous system. Two groups of mice were tested. The first group of mice were fed daily for 5 days with 1 mg nBSA on microspheres coated with the Eudragit L30D. A second group was fed with the same amount of nBSA in soluble form. The group which was fed the coated microspheres showed a significant IgG antiBSA antibody titers while sera from mice fed nBSA in water solution showed only borderline response. These results are shown in FIG. 9.

EXAMPLE 8

Immunogenicity of Microspheres Containing Diphtheria Toxoid in Mice

Figure 10:
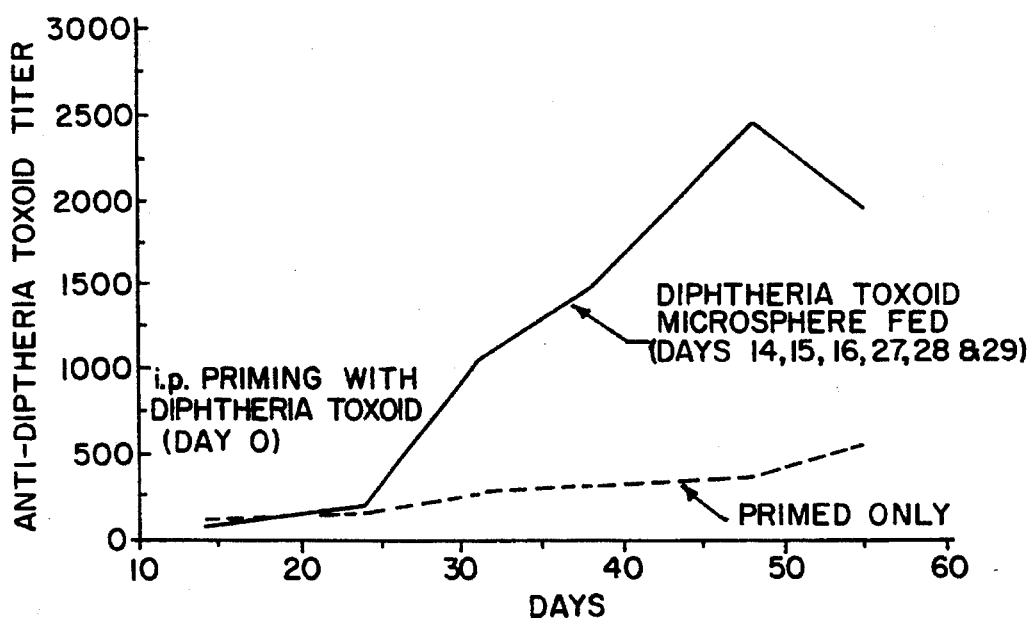
FIG. 10 is a graph showing the anti-diphtheria toxoid titer in mice primed with diphtheria toxoid and fed enteric coated diphtheria toxoid microspheres primed with diphtheria toxoid without subsequent immunization.

Diphtheria toxoid was obtained from Lederle Laboratories, Pearl River. Six ml of the toxoid concentrate and 3 gm PVP suspended in 200 ml water were coated onto nonpareils and subsequently coated with a solution of 33.3 gm Eudragit L30D (30% solids) and 1.1 gm triethyl citrate. Microspheres were orally administered to mice. Microspheres containing 1 Lf diphtheria toxoid were fed on days 14, 15, 16, and 27, 28, and 29.) All mice (DF females 6–8 weeks old) were immunized i.p. with 1 Lf units of diphtheria toxoid in alum on day 0. Mice fed diphtheria toxoid microspheres produced significantly increased levels of specific antibodies than mice that were just primed (FIG. 10).

EXAMPLE 9

Adjuvant Effect of Alum in Microspheres

Figure 11:
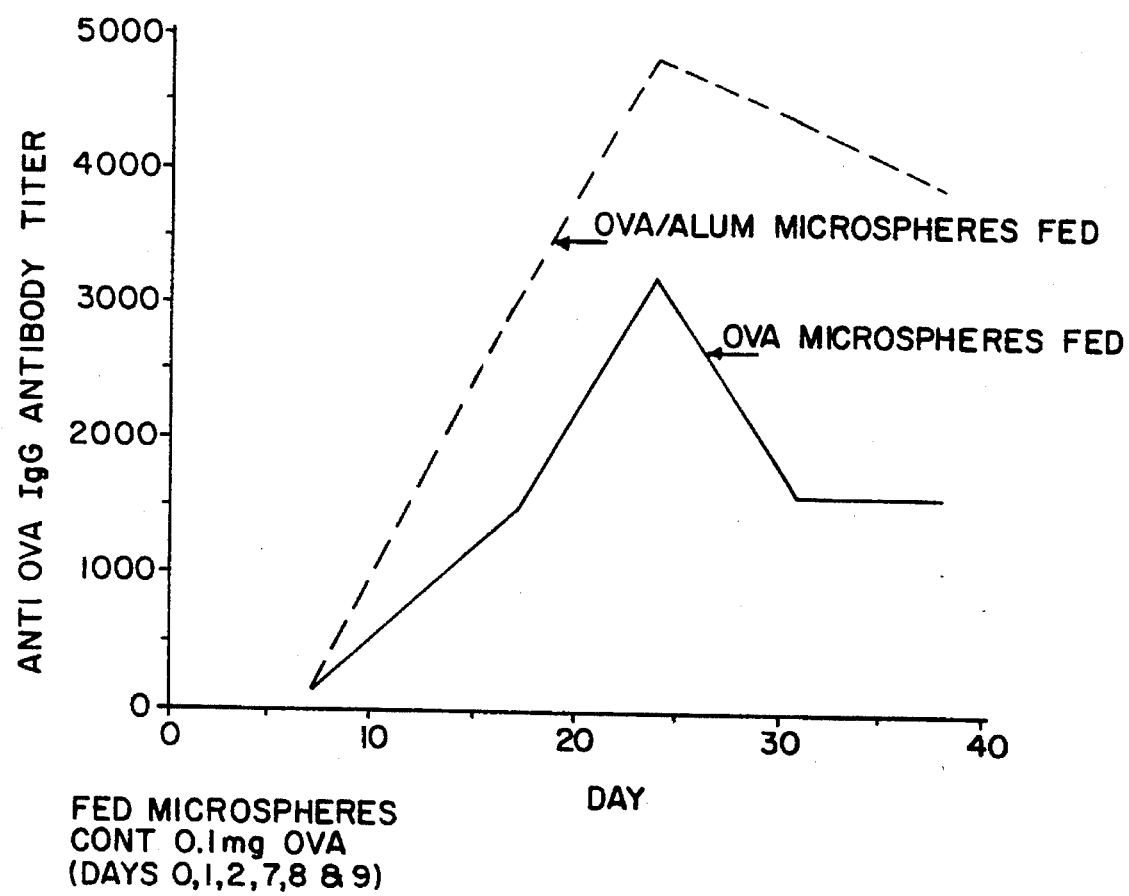
FIG. 11 is a graph showing IgG antibody titers of mice fed enteric coated microspheres containing OVA or OVA and aluminum hydroxide.

The addition of aluminum hydroxide to a therapeutic protein (OVA) was tested. OVA was adsorbed on aluminum hydroxide by mixing the protein with the aluminum hydroxide in a ratio 1:2 by weight. The mixture was suspended in water and sprayed on non-pareils which were then enteric coated with Eudragit L30D. The conditions of encapsulation were the same as described earlier for OVA encapsulation. The immune response in 6 week old BDF mice to encapsulated OVA-aluminum hydroxide mixture was significantly greater than observed for encapsulated OVA prepared without aluminum hydroxide as determined by measurement of antiOVA IgG antibody titers (FIG. 11).

The present invention provides an oral treatment modality for a wide variety of conditions such as common allergies as well as bacterial and viral infections. Denaturation of the therapeutic protein is avoided when coating the protein with an enteric coat. The prevention of denaturation was demonstrated by measuring immune responses to these proteins against native, unmodified antigens. If the antigen were denatured during encapsulation, antibody produced against this molecule would not react with the native antigen. Furthermore, the coating provides protection against low pH and enzymatic degradation enabling delivery of the intact molecule into small intestine. These beneficial effects of orally administered antigens are evidenced by induction of IgG immune response both in humans and animals and further confirmed by the therapeutical effects with respect to ragweed allergy. The efficacy of the immune response can be further enhanced by the addition of an aluminum compound.

The preceding has been a description of the present invention along with the preferred method currently known of practicing the invention. While there are many minor modifications that can be made without departing from the scope of the present invention, the scope of the present invention should be defined by the appended claims wherein

We claim:

1. An orally administrable therapeutic composition comprising an immunogen microencapsulated in the complete absence of organic solvents with a water based enteric coating wherein said immunogen has an immunotherapeutic effect against an allergen in a warm blood animal.

2. The composition claimed in claim 1 wherein said enteric coating is a water based emulsion of a methacrylic acid copolymer.

3. A composition according to claim 1 wherein said immunogen is an allergen selected from the group consisting of pollen allergens, dust, mites, food allergens, animal danders and insect venoms.

4. A composition according to claim 3 wherein said immunogen is a pollen allergen selected from the group consisting of ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple and elm.

5. An orally administrable therapeutic composition consisting essentially of an immunogen and at least one of an adjuvant which increases immunogenicity of said immunogen, a stabilizing sugar selected from the group consisting of lactose, trehalose and mannitol and a binding agent, microencapsulated in the complete absence of organic solvents with a water based enteric coating wherein said immunogen has an immunotherapeutic effect against an allergen in a warm blooded animal.

6. The composition of claim 5 wherein said binding agent is polyvinylpyrrolidone.

7. The composition of claim 5 wherein said adjuvant is selected from the group consisting of aluminum sulfate and aluminum hydroxide.

8. A composition according to claim 5 wherein said immunogen is an allergen selected from the group consisting of pollen allergens, dust, mites, food allergens, animal danders and insect venoms.

9. A composition according to claim 8 wherein said immunogen is a pollen allergen selected from the group consisting of ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple and elm.

10. An orally administrable therapeutic composition consisting essentially of a ragweed allergen and optionally an adjuvant, a stabilizing sugar and a binding agent microencapsulated in the complete absence of organic solvents with a water based enteric coating wherein said composition is therapeutically effective at a dosage of less than or equal to 35 Arab a 1 units administered daily.

11. The composition claimed in claim 10 wherein said enteric coating is a water based emulsion ethylacrylate methacrylic acid copolymer.

12. The therapeutic composition claimed in claim 31 wherein said adjuvant is selected from the group consisting of aluminum sulfate and aluminum hydroxide.

13. The orally administered therapeutic composition claimed in claim 10 wherein said binding agent is polyvinylpyrrolidone.

14. An orally administrable composition comprising an immunogen microencapsulated on particles of a pharmaceutically inert material having a first coating comprising said immunogen and a second coating comprising said enteric coating wherein said immunogen has an immunotherapeutic effect against an allergen in a warm blooded animal.

15. A composition according to claim 14 wherein said immunogen is an allergen selected from the group consisting of pollen allergens, dust, mites, food allergens, animal danders and insect venoms.

16. A composition according to claim 15 wherein said immunogen is a pollen allergen selected from the group consisting of ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple and elm.

17. The composition of claim 14 wherein said first coating further comprises at least one of a stabilizing sugar and a binding agent to bind said allergen to said particles.

18. The composition of claim 14 wherein said second coating further comprises a plasticizer.

19. The composition of claim 17 wherein said stabilizing sugar comprises trehalose.

20. The composition of claim 17 wherein said stabilizing sugar comprises trehalose.

21. The composition of claim 17 wherein said binding agent comprises polyvinylpyrrolidone.

22. The composition of claim 18 wherein said plasticizer comprises triethyl citrate.

23. An orally administrable composition comprising at least one immunogen microencapsulated in the complete absence of organic solvents with a water based enteric coating, wherein said immunogen is microencapsulated on particles of a pharmaceutically inert material with a first coating comprising
said immunogen,
lactose or trehalose, and
polyvinylpyrrolidone, and a second coating comprising
said enteric coating and
triethyl titrate wherein said immunogen has an immunotherapeutic effect against an allergen in a warm blooded animal.

24. A composition according to claim 23 wherein said immunogen is an allergen selected from the group consisting of pollen allergens, dust, mites, food allergens, animal danders and insect venoms.

25. A composition according to claim 25 wherein said immunogen is a pollen allergen selected from the group consisting of ragweed, rye, June grass, orchard grass, sweet vernal grass, red top grass, timothy grass, yellow dock, wheat, corn, sagebrush, blue grass, California annual grass, pigweed, Bermuda grass, Russin thistle, mountain cedax, oak, box elder, sycamore, maple and elm.

* * * * *